US00PP11064P

United States Patent [19]

Troutner

[11] Patent Number: Plant 11,064

[45] Date of Patent: Sep. 21, 1999

[54] **MYOPORUM PLANT VARIETY NAMED *MYOPORUM PARVIFOLIUM* 'ROBUSTUM'**

[76] Inventor: John C. Troutner, 27 South St., San Luis Obispo, Calif. 93401

[21] Appl. No.: 08/925,379

[22] Filed: Sep. 8, 1997

[51] Int. Cl.[6] ..... A01H 5/00

[52] U.S. Cl. ..... Plt./226

[58] Field of Search ..... Plt./54.1, 226

*Primary Examiner*—Elizabeth Kemmerer

*Attorney, Agent, or Firm*—Christie, Parker & Hale, LLP

[57] ABSTRACT

A new and distinct rapidly growing Myoporum plant variety of prostrate form.

1 Drawing Sheet

BACKGROUND OF THE INVENTION

This invention relates to a new and distinct variety of Myoporum which was discovered as a seedling in a cultivated planting of the variety Myoporum in the city and county of San Luis Obispo, Calif. The varietal denomination of the new variety is *Myoporum parvifolium* 'Robustum'.

There are four known forms of prostrate Myoporum and the new variety is distinctly different from each of them. '*Myoporum parvifolium*' is a somewhat vine-like prostrate ground cover which reaches a height of only a few inches and a width of about 12 to 15 feet. The leaves are approximately ⅛ inch wide by ¾ inch long. *Myoporum parvifolium* 'Putah Creek' grows slightly larger than the species with leaves about ¼ inch wide by about 1½ inches long and the foliage is considerably lighter, i.e. more yellow, in color than the species. Myoporum 'South Coast' is a large spreading shrub growing to 3 feet tall and 10 to 15 feet wide. The leaves are glossy, medium green and about ½ inch wide by 2 inches long. Myoporum 'pacificum' is a wide spreading shrub more than 3 feet tall and up to 30 feet wide with dark green leaves 1 inch wide by 3 inches long (U.S. Plant Pat. No. 4,560).

SUMMARY OF THE INVENTION

Among the novel characteristics possessed by the new variety which distinguish it from other varieties of which I am aware are: 1) a fast growing plant with extremely dense foliage that gives the plant a compact appearance; 2) a spidery plant appearance when viewed from the side; 3) glossy upper and lower leaf surfaces; and 4) lanceolate leaves with serrulate margins about ½ inch wide and about 2 to 2½ inches long showing little variation on the plant.

Plants planted in the ground from a one gallon container Apr. 13, 1996 had a plant width (spread) of about 8 inches. As of Jul. 4, 1998, the plant's width was about 12 feet and the height was about 30 inches.

The new variety of Myoporum is very well suited for use as ground cover on banks or flat areas. It is also very useful for erosion control and site beautification because of its dense foliage and quick growth.

Asexual reproduction by cuttings of the new variety in Slo, Calif., has demonstrated that the combination of characteristics as described herein for the new variety are firmly fixed and are retained through successive generations of asexual reproduction.

BRIEF DESCRIPTION OF ILLUSTRATIONS

The accompanying two illustrations describe stem and foliage of the new variety in color as true as is reasonably possible to make in an illustration of this nature.

In one illustration, the new variety shown on the right, is compared with stem and foliage from left to right, respectively, *Myoporum 'parvifolium', Myoporum parvifolium* 'Putah Creek', Myoporoum 'South Coast', and *Myoporum 'pacificum'*.

In the other illustration the new variety is shown alone and the prostrate growth habit is illustrated.

DESCRIPTION OF THE NEW VARIETY

The following observations and descriptions are of specimens of the new variety grown outdoors in San Luis Obispo County, Calif., in the month of July. Variation in environmental cultural climatic practices may affect phenotypic expression.

PLANT

1. General growth habit: Vigorously growing, prostrate, copiously branching, foliage very dense.
2. Typical dimensions: After about 15 months from planting, width about 12 feet, height about 30 inches.
3. Foliage:
   - *Leaf description.*—Simple, lanceolate. Width: About ½ inch. Length: About 2 inches to 2½ inches. Apex: Acuminate. Base: Attenuate, short petiolate to sessile. Margins: Mostly profusely serrulate. Quantity: Very numerous foliage. overall; one leaf per node, alternate.
   - *Color.*—Mature leaf surfaces: Upper side is olive green, near 137B, lower side is yellow green. Immature leaf surfaces: Upper side is near 137A, lower side is a lighter yellow green that of the mature leaves.
   - *Texture.*—Mature leaves: Upper and lower surfaces glabrous, glossy, rough with many glandular dots. Younger leaves: Essentially the same in texture as the older ones with the exception that the glandular dots are not as pronounced. Aspect: Midvein raised and pronounced on the lower surface; glandular dots pronounced along the midvein; leaves are reflexed downward, and folded upward along the midvein; the folding is more definite in immature leaves. Rooting: Taprooted with root branches growing quickly as with the stem.

4. Disease and insect resistance: No apparent insect or disease problems.
5. Flowers: The calyx is five toothed. The corolla is regular, sympetalous, 5 lobed, white with purple dots particularly near the base, bell shaped, about ¾ inch in diameter. The flowers are perfect, stamens 4, inserted on the throat of the corolla. The flowers are in clusters but are not particularly showy. The number of locules in the ovary varies. The fruit is a few-seeded reddish purple drupe, about ½ inch long, oblong.

I claim:

1. A new and distinct Myoporum plant, substantially as shown and described, characterized by prostrate form, dense growth and fast growing ability.

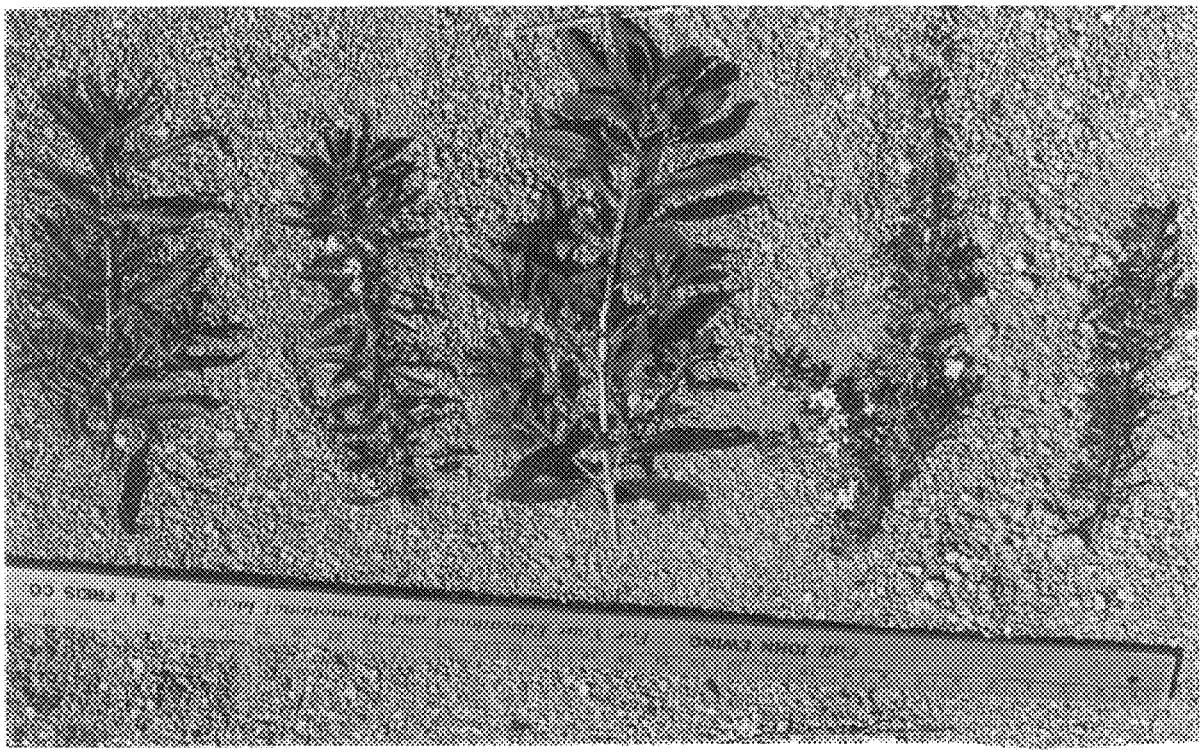
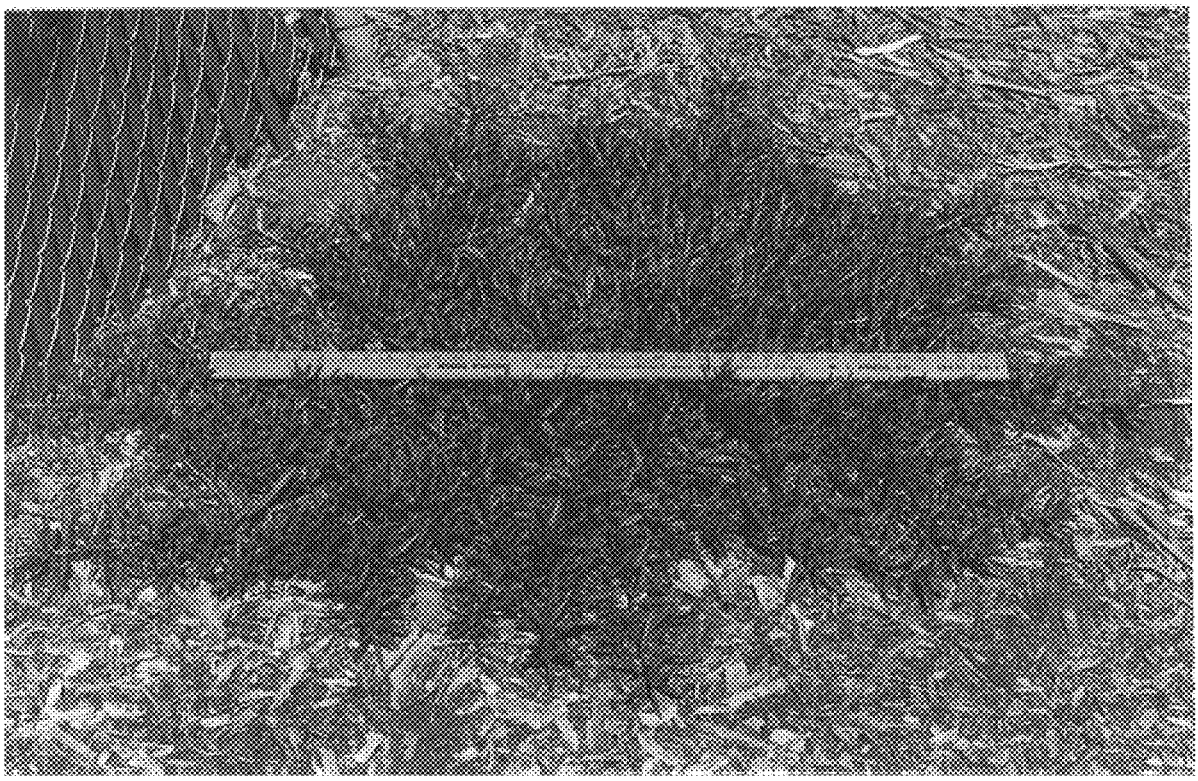

* * * * *